(12) United States Patent
Sagel et al.

(10) Patent No.: US 6,582,708 B1
(45) Date of Patent: *Jun. 24, 2003

(54) TOOTH WHITENING SUBSTANCE

(75) Inventors: Paul Albert Sagel, Mason, OH (US); Sue Ellen Bernheim, Blue Ash, OH (US); Lesle Marie Goodhart, Blanchester, OH (US); Hooman Shahidi, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/605,774

(22) Filed: Jun. 28, 2000

(51) Int. Cl.$^7$ .......................... A61K 6/02; A61K 7/16; A61K 7/20; A61K 33/40
(52) U.S. Cl. .......................... 424/401; 424/49; 424/53; 424/613; 424/54
(58) Field of Search .......................... 424/401, 49, 53, 424/54, 613

(56) References Cited

U.S. PATENT DOCUMENTS

| | | | |
|---|---|---|---|
| 2,835,628 A | 5/1958 | Saffir .......................... 433/39 |
| 3,070,102 A | 12/1962 | MacDonald .......................... 15/104.94 |
| 3,625,215 A | 12/1971 | Quisling .......................... 433/25 |
| 3,657,413 A | 4/1972 | Rosenthal et al. |
| 3,688,406 A | 9/1972 | Porter et al. .......................... 433/217.1 |
| 3,754,332 A | 8/1973 | Warren, Jr. .......................... 433/217.1 |
| 3,844,286 A | 10/1974 | Cowen |
| 3,902,509 A | 9/1975 | Tundermann et al. .......................... 433/142 |
| 3,955,281 A | 5/1976 | Weitzman .......................... 433/25 |
| 3,964,164 A | 6/1976 | Kesselgren |
| 3,972,995 A | 8/1976 | Tsuk et al. |
| 4,138,314 A | 2/1979 | Patil et al. |
| 4,138,814 A | 2/1979 | Weitzman .......................... 433/215 |
| 4,182,222 A | 1/1980 | Stahl |
| 4,211,330 A | 7/1980 | Strock .......................... 205/581 |
| 4,307,075 A | 12/1981 | Martin |
| 4,324,547 A | 4/1982 | Arcan et al. .......................... 433/71 |
| 4,335,731 A | 6/1982 | Bora, Jr. .......................... 433/216 |
| 4,363,843 A | 12/1982 | Crofts |
| 4,376,628 A | 3/1983 | Aardse .......................... 433/80 |
| 4,428,373 A | 1/1984 | Seid et al. .......................... 604/77 |
| 4,431,631 A | 2/1984 | Clipper et al. .......................... 424/53 |
| 4,518,721 A | 5/1985 | Dhabhar et al. .......................... 523/120 |
| 4,522,805 A | 6/1985 | Gordon .......................... 424/52 |
| 4,522,806 A | 6/1985 | Muhlemann et al. .......................... 424/52 |
| 4,528,180 A | 7/1985 | Schaeffer .......................... 424/52 |
| 4,537,778 A | 8/1985 | Clipper et al. .......................... 424/53 |
| 4,544,354 A | 10/1985 | Gores et al. .......................... 433/52 |
| 4,554,154 A | 11/1985 | White |
| 4,557,692 A | 12/1985 | Chorbajian .......................... 433/215 |
| 4,560,351 A | 12/1985 | Osborne .......................... 433/80 |
| 4,568,536 A | 2/1986 | Kronenthal et al. .......................... 424/435 |
| 4,592,487 A | 6/1986 | Simon et al. .......................... 222/194 |
| 4,592,488 A | 6/1986 | Simon et al. .......................... 222/94 |
| 4,661,070 A | 4/1987 | Friedman .......................... 433/203.1 |
| 4,687,663 A | 8/1987 | Schaeffer .......................... 424/52 |
| 4,696,757 A | 9/1987 | Blank et al. .......................... 252/186.29 |
| 4,713,243 A | 12/1987 | Schiraldi et al. |
| 4,728,291 A | 3/1988 | Golub .......................... 433/215 |
| 4,741,700 A | 5/1988 | Barabe .......................... 433/229 |
| 4,741,941 A | 5/1988 | Englebert et al. .......................... 428/71 |
| 4,755,385 A | 7/1988 | Etienne et al. .......................... 424/687 |
| 4,755,386 A | 7/1988 | Hsiao et al. |
| 4,770,634 A | 9/1988 | Pellico .......................... 433/217.1 |
| 4,786,253 A | 11/1988 | Morals .......................... 433/60 |
| 4,788,052 A | 11/1988 | Ng et al. .......................... 424/53 |
| 4,799,888 A | 1/1989 | Golub .......................... 433/215 |
| 4,812,308 A | 3/1989 | Winston et al. .......................... 424/52 |
| 4,828,112 A | 5/1989 | Friedland et al. |
| 4,839,156 A | 6/1989 | Ng et al. |
| 4,839,157 A | 6/1989 | Ng et al. |
| 4,849,213 A | 7/1989 | Schaeffer |
| RE33,093 E | 10/1989 | Shiraldi et al. |
| 4,895,721 A | 1/1990 | Drucker |
| 4,900,552 A | 2/1990 | Sanvordeker et al. |
| 4,900,554 A | 2/1990 | Yanagibashi et al. |
| 4,902,227 A | 2/1990 | Smith |
| 4,919,615 A | 4/1990 | Croll |
| 4,968,251 A | 11/1990 | Darnell |
| 4,971,782 A | 11/1990 | Rudy et al. |
| 4,972,946 A | 11/1990 | Whittaker |
| 4,980,152 A | 12/1990 | Frazier et al. |
| 4,983,379 A | 1/1991 | Schaeffer |
| 4,983,381 A | 1/1991 | Zaragoza |

(List continued on next page.)

FOREIGN PATENT DOCUMENTS

| CA | 1209761 | 8/1986 |
|---|---|---|
| CA | 2078960 | 10/1993 |
| CA | 2095445 | 7/1995 |
| CA | 2000040 | 10/1995 |

(List continued on next page.)

OTHER PUBLICATIONS

Dentistry Today 'Buyers' Guide to Whitening Systems, pp. 125, 126, 130, 132, 134; (Dec. 1997).

Dentistry Today 'Buyers' Guide; "Opalescence" Tooth Whitening Gel "Opalescence" Xtra Ultradent Products, Inc.; (Dec. 1997).

Ultradent Products, Inc. Online; Base Plate Tray Sheets; (Jan. 29, 1998, Jun. 23, 1997, Mar. 16, 1997) downladed 4–2002.

(List continued on next page.)

Primary Examiner—Frederick Krass
Assistant Examiner—Donna Jagoe
(74) Attorney, Agent, or Firm—James C. Vago

(57) ABSTRACT

The present invention relates to a product comprising tooth whitening substance which comprises a high concentration of water, a peroxide, a gelling agent, and carrier materials. The tooth whitening substance will remain stable when stored as a thin layer. The present invention also relates to a method of storage of a tooth whitening substance and a method producing a stable thin layer of tooth whitening substance on a strip of material. Additionally, the present invention relates to the benefits obtained from the tooth whitening composition.

41 Claims, No Drawings

U.S. PATENT DOCUMENTS

| | | |
|---|---|---|
| 4,988,500 A | 1/1991 | Hunter et al. |
| 4,990,089 A | 2/1991 | Munro |
| 5,059,120 A | 10/1991 | Lee |
| 5,059,417 A | 10/1991 | Williams et al. |
| 5,076,791 A | 12/1991 | Madray, Jr. |
| 5,084,268 A | 1/1992 | Thaler |
| 5,098,303 A | 3/1992 | Fischer |
| 5,122,365 A | 6/1992 | Murayama |
| 5,165,424 A | 11/1992 | Silverman |
| 5,166,233 A | 11/1992 | Kuroya et al. |
| RE34,196 E | 3/1993 | Munro |
| 5,211,559 A | 5/1993 | Hart et al. |
| 5,234,342 A | 8/1993 | Fischer |
| 5,256,402 A | 10/1993 | Prencipe et al. |
| 5,290,566 A | 3/1994 | Schow et al. |
| 5,310,563 A | 5/1994 | Curtis et al. |
| 5,320,831 A | 6/1994 | Majeti et al. |
| 5,326,685 A | 7/1994 | Gaglio et al. |
| 5,340,314 A | 8/1994 | Tarvis |
| 5,340,581 A | 8/1994 | Tseng et al. |
| 5,356,291 A | 10/1994 | Darnell |
| 5,376,006 A | 12/1994 | Fischer |
| 5,380,198 A | 1/1995 | Suhonen |
| 5,401,495 A | 3/1995 | Murayama |
| 5,409,631 A | 4/1995 | Fischer |
| 5,425,953 A | 6/1995 | Sintov et al. |
| 5,438,076 A | 8/1995 | Friedman et al. |
| 5,472,704 A | 12/1995 | Santus et al. |
| 5,505,933 A | 4/1996 | Norfleet et al. |
| 5,522,726 A | 6/1996 | Hodosh |
| 5,560,379 A | 10/1996 | Pieczenik |
| 5,565,190 A | 10/1996 | Santalucia et al. ............ 424/53 |
| 5,575,654 A | 11/1996 | Fontenot |
| 5,575,655 A | 11/1996 | Darnell |
| 5,611,687 A | 3/1997 | Wagner |
| 5,616,027 A | 4/1997 | Jacobs et al. |
| 5,620,322 A | 4/1997 | Lococo |
| 5,626,866 A | 5/1997 | Ebert et al. |
| 5,631,000 A | 5/1997 | Pellico et al. |
| 5,639,445 A | 6/1997 | Curtis et al. |
| 5,645,428 A | 7/1997 | Yarborough |
| 5,662,758 A | 9/1997 | Hamilton et al. |
| 5,678,273 A | 10/1997 | Porcelli |
| 5,707,235 A | 1/1998 | Knutson |
| 5,707,736 A | 1/1998 | Levy et al. |
| 5,713,738 A | 2/1998 | Yarborough |
| 5,723,132 A | 3/1998 | Tseng et al. |
| 5,725,843 A | 3/1998 | Fischer |
| 5,746,598 A | 5/1998 | Fischer |
| 5,759,037 A | 6/1998 | Fischer |
| 5,759,038 A * | 6/1998 | Fischer ...................... 433/215 |
| 5,770,105 A | 6/1998 | Fischer |
| 5,770,182 A | 6/1998 | Fischer |
| 5,780,045 A | 7/1998 | McQuinn et al. |
| 5,819,765 A | 10/1998 | Mittiga |
| 5,827,591 A | 10/1998 | Blok et al. |
| 5,846,058 A | 12/1998 | Fischer ........................ 433/37 |
| 5,851,512 A | 12/1998 | Fischer |
| 5,855,870 A | 1/1999 | Fischer |
| 5,858,332 A | 1/1999 | Jensen et al. |
| 5,863,202 A | 1/1999 | Fontenot |
| 5,879,591 A | 3/1999 | Nagoh et al. ............... 252/586 |
| 5,879,691 A | 3/1999 | Sagel et al. |
| 5,891,453 A * | 4/1999 | Sagel et al. ................. 424/401 |
| 5,894,017 A | 4/1999 | Sagel et al. ................. 424/401 |
| 5,922,307 A | 7/1999 | Montgomery |
| 5,953,885 A | 9/1999 | Berman et al. |
| 5,968,633 A | 10/1999 | Hamilton et al. |
| 5,980,249 A | 11/1999 | Fontenot |
| 5,985,249 A | 11/1999 | Fischer |
| 5,989,569 A | 11/1999 | Dirksing et al. ............ 424/401 |
| 6,036,943 A | 3/2000 | Fischer ........................ 424/49 |
| 6,045,811 A | 4/2000 | Dirksing et al. ............ 424/401 |
| 6,086,855 A | 7/2000 | Fischer |
| 6,094,889 A | 8/2000 | Van Loon et al. |
| 6,096,328 A * | 8/2000 | Sagel et al. ................. 424/401 |
| 6,106,293 A | 8/2000 | Wiesel |
| 6,126,443 A | 10/2000 | Burgio |
| 6,136,297 A | 10/2000 | Sagel et al. |
| 6,142,780 A | 11/2000 | Burgio |
| 6,155,832 A | 12/2000 | Wiesel |
| 6,182,420 B1 | 2/2001 | Berman et al. |
| 6,274,122 B1 | 8/2001 | McLaughlin |
| 6,277,458 B1 | 8/2001 | Dirksing et al. |
| 6,309,625 B1 | 10/2001 | Jensen et al. |
| 6,322,360 B1 | 11/2001 | Burgio |

FOREIGN PATENT DOCUMENTS

| | | |
|---|---|---|
| CA | 2162536 | 5/1996 |
| CA | 2162812 | 5/1996 |
| CA | 2162885 | 5/1996 |
| DE | 1104116 | 4/1961 |
| DE | 2330869 | 1/1975 |
| EP | 0 063 604 | 4/1982 |
| EP | 0 200 508 | 12/1986 |
| EP | 0 252 459 | 1/1988 |
| EP | 0 381 194 | 8/1990 |
| EP | 0763358 A1 | 9/1996 |
| EP | 0 763 358 A1 | 3/1997 |
| GB | 1142325 | 2/1969 |
| GB | 2108841 | 5/1983 |
| JP | 60005159 | 1/1955 |
| JP | 60005160 | 1/1985 |
| JP | 63005756 | 1/1988 |
| JP | 6354318 | 3/1988 |
| JP | 2250826 | 10/1990 |
| JP | 3-264522 | 11/1991 |
| JP | 3-264523 | 11/1991 |
| RU | 2075965 C1 | 9/1994 |
| WO | WO88/06879 | 9/1988 |
| WO | WO95/05416 | 2/1995 |
| WO | WO95/24872 | 9/1995 |
| WO | WO97/25968 | 7/1996 |
| WO | WO 99/27895 | 6/1999 |

OTHER PUBLICATIONS

S.M. Newman, et al., "Tray–Forming Technique for Dentist–Supervised Home Bleaching", *Quintessence International*, 1995, pp. 447–453, vol. 26, No. 7.

G. McLaughlin, et al., "Materials" and "Clinical Techniques", *Color Atlas of Tooth Whitening*, 1991, pp. 35–38 & 45–50, Ishiyaku EuroAmerica, Inc.

R.E. Goldstein, et al., "Chemistry of Bleaching", *Complete Dental Bleaching*, 1995, pp. 25–32 & 90–97, Quintessence Publishing Co, Inc.

V.B. Haywood, et al., "Nightguard Vital Bleeching", *Quintessence International*, 1989, vol. 20, No. 3, pp. 173–176, 19th International Meeting on Dental Implants and Transplants, Bologna, Italy.

V.B. Haywood, "History, Safety, and Effectiveness of Current Bleaching Techniques and Applications of the Nightguard Vital Bleaching Technique", *Quintessence International*, 1992, vol. 23, No. 7, pp. 471–488.

V.B. Haywood, "Nightguard Vital Bleaching", *Dentistry Today*, 1997, pp. 86–91.

V.B. Haywood, "Nightguard Vital Bleaching: Current Concepts and Research", *JADA*, 1997, vol. 128, pp. 19S–25S.

"Tooth Bleaching, Home–Use Products", *Clinical Research Associates Newsletter*, 1989, vol. 3, Issue 12.

Ralph H. Leonard Jr., et al, "Risk factors for developing tooth sensitivity and gingival irritation associated with nightguard vital bleaching", *Esthetic Dentistry*, 1997, vol. 28, No. 8, pp. 527–534.

Van B. Haywood, et al, "Nightguard vital bleaching: how safe is it?", *Esthetic Dentistry*, 1991, vol. 22, No. 7, pp. 515–523.

Van B. Haywood, "History, safety and effectiveness of current bleaching techniques and applications of the nightguard vital bleaching technique", *Esthetic Dentistry*, 1992, vol. 23, No. 7, pp. 471–488.

Van B. Haywood, "Bleaching of vital and notvital teeth", *Periodontology and Restorative Dentistry*, 1992, pp. 142–149.

Van B. Haywood, "Nightguard vital bleaching, a history and products update: Part 1", *Esthestic Dentistry Update*, 1991, vol. 2, No. 4, pp. 63–66.

Van B. Haywood, "Nightguard vital bleaching, a history and products update: Part 2", *Esthetic Dentistry Update*, 1991, vol. 2, No. 5, pp. 82–85.

Claudia Paula Drew, "Teeth Bleaching . . . a Vital technique for you to know", 1988, Sep./Oct., pp. 23–25.

Van Benjamin Haywood, "Overview and Status of Mouthguard Bleaching" *Journal of Esthetic Dentistry*, 1991, vol. 3, No. 5, pp. 157–161.

Van B. Haywood, "Nightguard vital bleaching: current information and research", *Esthetic Denstistry Update*, 1990, vol. 1, No. 2, pp. 20–25.

Carolyn F. G. Wilson, et al., "Color change following vital bleaching of tetracycline–stained teeth" *Pediatric Dentistry*, 1985, vol. 7, No. 3, pp. 205–208.

"Tooth Bleaching, Home–Use Products", *Clinical Research Associates Newsletter*, 1989, pp. 1–4.

Sue Ellen Richardson, "Home bleaching: effectiveness, history, technique, bleaches, cost and safety" *The Journal of the Greater Houston Dental Society*, 1989, pp. 22–26.

Van B. Haywood, "Nightguard vital bleaching", *Dentistry Today*, 1997, pp. 88–91.

Van B. Haywood, "The food and drug administration and its influence on home bleaching", *ADA*, 1993, pp. 12–18.

Van B. Haywood, "Efficacy of foam liner in 10% carbamide peroxide bleaching technique", *Esthetic Dentistry*, 1993, vol. 24, No. 9, pp. 663–666.

Christopher J. Woolverton, "Toxicity of two carbamide peroxide products used in nightguard vital bleaching", *American Journal of Dentistry*, 1993, vol. 6, No. 6, pp. 310–314.

Van B. Haywood, "Response of normal and tetracycline–stained teeth with pulp–size variation to nightguard vital bleaching", *Journal of Esthetic Dentistry*, 1994, vol. 6, No. 3, pp. 109–114.

Ralph H. Leonard, et al, "Salivary pH changes during 10% carbamide peroxide bleaching" *Dental Research*, 1994, vol. 25, No. 8, pp. 547–550.

Ralph H. Leonard, et al, "Changes in pH of plaque and 10% carbamide peroxide solution during nightguard vital bleaching treatment" *Esthetic Dentistry*, 1994, vol. 25, No. 12, pp. 819–823.

Van B. Haywood, "Historical development of whiteners: clinical safety and efficacy", *Aesthetics*, 1997, pp. 98–104.

Van B. Haywood, "Considerations and variations of dentist–prescribed,home–applied vital tooth–bleaching techniques", *Compend Contin Educ Dent*, 1994, Suppl.No. 17, pp. s616–s621.

Van B. Haywood, "Effectiveness, side effects and long–term status of nightguard vital bleaching", *JADA*, 1994, vol. 125, pp. 1219–1226.

James W. Curtis, et al, "Assessing the effects of 10 percent carbamide peroxide on oral soft tissues", *JADA*, 1996, vol. 127, pp. 1218–1223.

Fonda G. Robinson, et al, "Effect of 10 percent carbamide peroxide on color of provisional restoration materials", *JADA*, 1997, vol. 128, pp. 727–731.

Van B. Haywood, "Nightguard vital bleaching: current concepts and research", *JADA*, 1997, vol. 128, pp. 19s–25s.

Van B. Haywood, "Commonly asked questions about nightguard vital bleaching", *IDA Journal*, 1993, pp. 28–33.

Van B. Haywood, "Commonly asked questions about nightguard vital bleaching", *The Dental Assistant*, Mar./Apr. 1996, pp. 6–12.

M.S. McCracken, "Demineralization effects of 10 percent carbamide peroxide", *Journal of Dentistry*, 1996, vol. 24, No. 6, pp. 395–398.

Van B. Haywood, "Efficacy of six months of nightguard vital bleaching of tetracycline–stained teeth", *Journal of Esthetic Dentistry*, 1997, vol. 9, No. 1, pp. 13–19.

Van B. Haywood, "Achieving, maintaining and recovering successful tooth bleaching", *Journal of Esthetic Dentistry*, 1996, vol. 8, No. 1, pp. 31–38.

Carl M. Russell, et al, "Dentist–supervised home bleaching with ten percent carbamide peroxide gel: a six month study", *Journal of Esthetic Dentistry*, 1996, vol. 8, No. 4, pp. 177–182.

Van B. Haywood, "Historical development of whiteners: clinical safety and efficacy", *Aesthetics*, Apr. 1997 update, pp. 98–104.

U.S. application Ser. No. 09/605,220, Sagel, et al., filed Jun. 28, 2000, 6710R2C.

U.S. application Ser. No. 09/864,772, Sagel, et al., filed May 24, 2001, 6710R2C2.

U.S. application Ser. No. 09/681,729, Sagel, et al., filed May 29, 2001, 6710R2C4.

U.S. application Ser. No. 09/825,733, Sagel, et al., filed Apr. 4, 2001, 8489.

U.S. application Ser. No. 09/864,686, Sagel, et al., filed May 24, 2001, 6710R2C3.

U.S. application Ser. No. 08/675,767, Goodhart, et al., filed Sep. 29, 2000, 8124R.

U.S. application Ser. No. 09/638,822, Sagel, et al., filed Aug. 14, 2000, 8205.

U.S. application Ser. No. 09/864,640, Sagel, et al., filed May 24, 2001, 7478C.

U.S. application Ser. No. 09/268,185, Sagel, et al., filed Mar. 15, 1999, 7478.

Schumb, W.C. "Hydrogen Peroxide", American Chemical Society Monograph Series, 1955, pp. 189–547.

Besner, E., et al., Practical Endodontics, 1994, pp. 7–15, 178–180; Mosby–Year Book, Inc.

* cited by examiner

TOOTH WHITENING SUBSTANCE

FIELD OF THE INVENTION

The present invention relates to products comprising a tooth whitening substance containing a high water content and the benefits of these products.

BACKGROUND OF THE INVENTION

Tooth whitening has become very popular over the past few years. More and more consumers are choosing to whiten their teeth. Options for tooth whitening include toothpastes, mouthrinses, chewing gums, in-office bleaching, and most commonly tooth whitening solutions used with a tray obtained either over-the-counter or from a dentist. The tooth whitening solutions contain a which bleach the teeth. This solution is placed into a dental tray in which a patient wears to bleach his or her teeth. Typically, the tooth whitening substance comes in a squeeze bottle, tube, or syringe.

Recently, a new delivery system for tooth whitening has been developed. It is described in U.S. Pat. No. 5,891,453; 5,879,591 and 5,894,017 all incorporated herein by reference. The new delivery system for tooth whitening is a strip of material. A tooth whitening substance is applied to the strip of material so that when the delivery system is placed on the surface of the teeth, the substance contacts the surface providing an active onto the surface. The substance will also provide adhesive attachment between the strip of material and the surface of the teeth to hold the delivery system in place for a sufficient amount of time to allow the active to act upon the surface. This system allows for many advantages for the user. It is low cost, disposable, has a customized fit for each user, easy to use, and will not interfere with the wearer's speech or appearance. Therefore, a consumer desiring to whiten their teeth may prefer this system over a traditional tooth whitening system containing a tray.

It is know that tooth whitening active materials may be difficult to keep stable for long periods of time. The most common dental bleaching agents are peroxides, which are known to be very reactive. To improve stability, a peroxide may be encapsulated, formulated in a two part composition, or stabilizers added to maintain peroxide levels. Generally, the peroxide compositions are stored in sealed containers. For example, Opalescence and Natural White are provided to consumers in a syringe or tube. The syringe facilitates stability by decreasing the surface area to volume ratio and pushing out all air from the peroxide containing composition.

The present inventors have discovered that a tooth whitening substance coated on a substrate is much more difficult to stabilize. This is because the tooth whitening substance is stored as a thin layer and not in a syringe or in bulk. There is much more surface area for the peroxide to react on or with the surface. Surface area to volume ratios higher than 0.6 millimeters$^{-1}$ are unique situations because the heterogeneous decomposition of hydrogen peroxide becomes a major contributor to the overall decomposition rate of the peroxide. As detailed in *Hydrogen Peroxide*, by Walter Schumb, it is reported that the decomposition rates of hydrogen peroxide solutions is roughly proportional to the surface area to volume ratio over a considerable range. As the surface area to volume ratio increases, the decomposition rate increases as well. In addition, the portion of the surface of a storage container exposed to the vapor phase may also contribute substantially to the overall decomposition observed.

Surprisingly, the present inventors have found that when stored in a high surface area to volume form, such as in a thin layer, the tooth whitening substance is more stable if a higher concentration of water is present. This is contrary to common belief as many references have suggested that peroxide compositions would be more stable with less water. For example, Colgate has several patents including U.S. Pat. No. 5,565,190 which disclose that if water is present in excess of 9%, the stability of the dentifrice which contains peroxide begins to be effected.

In other examples, U.S. Pat. No. 5,846,058 issued to Fischer discloses a high viscosity sustained release dental composition. The dental bleaching agent in this composition is carbamide peroxide. The water level content is from about 10% to about 60%. Several years later, a continuation-in-part application was filed by Fischer on a similar dental composition. This is issued as U.S. Pat. No. 6,036,943. In this patent, Fischer discloses that water is an optional ingredient and present in a range of from about 0% to about 50%. As thought by Fischer and others having ordinary skill in the art, it is commonly believed that lower levels of water in peroxide containing tooth whitening solutions are preferred.

It is an object of this invention to provide stable tooth whitening substances containing peroxide having high water contents. More specifically, the tooth whitening substance will remain stable when stored as a thin layer.

It has also been discovered by the present inventors that the high water containing tooth whitening substances provide some additional benefits to the consumer. The additional benefits include reduced tooth sensitivity both during and after tooth whitening, a lower number of transient white spots formed during and after tooth whitening, and a minimal loss of tooth whitening occurring immediately after tooth whitening. These benefits are observed when compared to tooth whitening achieved through a lower water content tooth whitening substance.

It is believed that the benefit observed may be due to the teeth being less dehydrated during whitening and consequently, less hydration of the teeth needing to occur after whitening. The dehydration of the teeth may cause temporary tooth sensitivity both during whitening and after whitening. Dehydration of the teeth may also cause white spots to form on the teeth creating a temporary uneven tooth whitening. The need for less hydration after tooth whitening may also contribute to keeping the teeth at the shade of white longer as the teeth do not need to be rehydrated.

It is also believed that applying the high water content tooth whitening substance on a strip of material versus a tray will also create less dehydration and consequently enhance the benefits described above. This is because a smaller amount of tooth whitening substance is used on a strip of material compared to the amount of tooth whitening substance that is typically used on a tray or other implement. Therefore, the lower amount of tooth whitening substance used may also contribute in less tooth dehydration.

It has been found that the consumer will experience less tooth sensitivity during and immediately after whitening their teeth with the high water containing tooth whitening substance as compared to lower water containing tooth whitening substances. Tooth sensitivity is described as the generalized occurrence of pain or aching in the teeth and/or the pain in the teeth caused by hot or cold stimulus, air movement, or tooth contact or pressure. Increased tooth sensitivity during and after tooth whitening is one of the common complaints among consumers who whiten their teeth. Generally, this increased tooth sensitivity is temporary and will subside shortly after tooth whitening is complete, such as after 2–4 days. This benefit of a reduced amount of increased tooth sensitivity is found among both consumers who report high sensitivity before tooth whitening and also among consumers who do not have highly sensitive teeth before beginning a tooth whitening program. Therefore, consumers who thought that their teeth were too sensitive to whiten their teeth may be able to use the present invention comfortably. Consumers with sensitive teeth are identified through self reported answers and/or by using a toothpaste designed for sensitive teeth. Increased tooth sensitivity is commonly measured by the consumers answering a question regarding increased tooth sensitivity. The frequency of the tooth sensitivity and the intensity of the tooth sensitivity can both be assessed. The reduced amount of increased tooth sensitivity can be from a lower number of consumers reporting increased tooth sensitivity during and/or after whitening, a lower frequency or occurrence of tooth sensitivity experienced by a consumer, or by a lower degree or intensity of tooth sensitivity reported by a consumer.

It has also been discovered that the higher water content tooth whitening composition will provide a more even tooth whitening than other common whitening systems. For example, a consumer whitening his teeth with the high water content tooth whitening substance will develop less white spots than a consumer who whitens his teeth with a lower water content tooth whitening substance. The white spots are defined as temporary or transient white or lighter color spots or areas on the tooth. The white spots can develop anywhere on the tooth, even along the edge of a tooth. Typically, the white spot is temporary and does not last for very long. It is believed that white spots disappear or fade when the tooth is rehydrated after whitening. The benefit of preventing temporary uneven tooth whitening from occurring through the creation of substantially no or a reduced number of white spots can be observed or counted through visual observation. The number of white spots can also be measured through photometric methods known in the art.

Additionally, the present inventors have found that the higher water content tooth whitening substance will provide a lower rate of whitening loss immediately after tooth whitening. Once tooth whitening is achieved, a minimal loss of tooth whitening will occur compared to lower water content tooth whitening substances. This will prevent the immediate tooth whitening loss commonly referred to as the "rebound effect" during the first few hours and days after tooth whitening. The prevention of immediate tooth whitening loss can be measured hours after tooth whitening is complete, such as one, two, four, eight, or twenty-four hours after tooth whitening, or days later, such as one, two, three, or seven days after tooth whitening. This benefit of maintaining the tooth whitening will occur in most all consumers. The benefit can be measured through visual observation in looking at the shade of the tooth, the use of a shade guide, or through photometric methods.

SUMMARY OF THE INVENTION

The present invention relates to a product comprising tooth whitening substance which comprises a high concentration of water, a peroxide, a gelling agent, and carrier materials. The tooth whitening substance will remain stable when stored as a thin layer. The present invention also relates to a method of storage of a tooth whitening substance and a method producing a stable thin layer of tooth whitening substance on a strip of material. Additionally, the present invention relates to the benefits obtained from the tooth whitening composition.

DETAILED DESCRIPTION OF THE INVENTION

The abbreviation "cm", as used herein, means centimeter. The abbreviation "mm", as used herein, means millimeter.

The term "thin layer", as used herein, means the physical formation or position of the tooth whitening substance. The thin layer of tooth whitening substance is generally on or in contact with a substrate. The thin layer of tooth whitening substance may be stored, coated, or spread on the substrate. The thin layer will generally be less than about 3 mm thick or deep. This measurement is taken by measuring from the substrate and up through the thin layer of tooth whitening substance. The thin layer of tooth whitening substance is from about 0.01 mm to about 3 mm thick, preferably from about 0.02 mm to about 2 mm thick, more preferably from about 0.05 mm to about 1 mm thick, and most preferably from about 0.07 mm to about 0.5 mm thick. The thin layer will also have an exposed surface area of the tooth whitening substance to volume of tooth whitening substance ratio of greater than about 0.6 millimeter$^{-1}$. Typically, the surface area to volume ratio is from about 0.6 to about 200 millimeter$^{-1}$, preferably from about 1 to about 100 millimeter$^{-1}$, more preferably from about 2 to about 40 millimeter$^{-1}$, and most preferably from about 4 to about 25 millimeter$^{-1}$. The surface area of the gel is measured as the total surface area of the substrate and the release liner, if used, which is in contact with the thin layer of tooth whitening substance. Generally, it is the top, side, and bottom surfaces of the tooth whitening substance, although the side is typically negligible. If a release liner or other material is placed on top of the thin layer of tooth whitening substance, the surface area contacting the release liner are included as the surface area measurement. If a release liner is not used, the surface area of the thin layer exposed to the air is included with the surface area of the thin layer exposed to the substrate. The volume of the tooth whitening substance is measured in cubic millimeters and is the amount of tooth whitening substance that forms the thin layer.

The term "bulk", as used herein, means that the tooth whitening substance is not stored as a thin layer. For example, bulk would mean that it is stored in any type of closed container such as a drum, tube, syringe, or jar having very little or no head space or air in the container and lower surface area exposure. The total amount, volume or weight, of substance stored is not relevant when determining if something is stored in bulk or a thin layer. For example, a syringe may contain less than 5 grams of substance.

The term "stable", as used herein, means that the peroxide in the tooth whitening substance maintains at least 80% of its original amount or concentration. This measurement is commonly taken when the tooth whitening substance is stored as a thin layer for about three months after manufacture. The time period begins after the tooth whitening substance is manufactured and formed as a thin layer. This measurement will be taken when the substance is stored at room temperature, approximately 25° C. Preferable, a stable tooth whitening substance will have a peroxide concentration of about 85% and more preferably about 90% of its original amount about three months after manufacture.

The term "storage" or "stored", as used herein, means the period of time after the tooth whitening substance is produced or manufactured until the consumer uses the tooth whitening substance. The storage of the tooth whitening substance is typically as a thin layer and on a substrate.

The term "product", as used herein, means the tooth whitening substance that is used for tooth whitening. The tooth whitening substance will be in the form of a thin layer.

Tooth Whitening Substance

The tooth whitening substance is a composition, compound, or mixture capable of influencing or effecting a desired change in appearance and/or structure of the surface it contacts. Examples of appearance and structural changes include, but are not necessarily limited to, whitening, stain bleaching, stain removal, plaque removal, and tartar removal. Preferably, the active is for the whitening of the tooth surfaces, enamel, and/or dentin.

The amount of substance applied to the teeth will depend upon the size of the delivery implement, concentration of the active, and the desired benefit. Generally, less than about 1 gram of substance is required. Preferably, from about 0.05 grams to about 0.5 grams and more preferably from about 0.1 gram to about 0.4 grams of the substance is used. The amount of substance per square cm of material is less than about 0.2 grams/cm$^2$, preferably from about 0.005 to about 0.1 grams/cm$^2$, and more preferably from about 0.01 grams/cm$^2$ to about 0.05 grams/cm$^2$. Preferably, the tooth whitening substance is homogeneous, uniformly and continuously coated onto a substrate. However, the substance may alternatively be a laminate or separated layers of components, an amorphous mixture of components, separate stripes or spots or other patterns of different components, or a combination of these structures.

The substance of the present invention can be in the form of a viscous liquid, paste, gel, solution, or other suitable form that can form a thin layer. Preferably, the tooth whitening substance will provide sufficient adhesion to the teeth. Preferably, the substance is in the form of a gel and this gel will form a thin layer on a substrate. The tooth whitening substance will have a viscosity of from about 200 to about 1,000,000 cps at low shear rates (approximately one seconds$^{-1}$). Preferably, the viscosity is from about 100,000 to about 800,000 cps, more preferably from about 150,000 to about 700,000 cps, and most preferably from about 300,000 to about 700,000 cps. The substance will also have a yield stress. Yield stress is the amount of force on the material before the material begins to move. The yield stress must be high enough so that the substance is able to form a thin layer and also to handle the disturbances caused by manufacturing, handling, and storage. The yield stress of the substance of the present invention is from about 2 Pascals to about 3000 Pascals, preferably from about 20 Pascals to about 2000 Pascals, more preferably from about 200 Pascals to about 1500 Pascals, and most preferably from about 400 Pascals to about 1200 Pascals.

Peroxides suitable for whitening include any material safe for use in the oral cavity which is a peroxide or produces a peroxide and provides bleaching or stain removal. Suitable peroxide compounds include hydrogen peroxide, calcium peroxide, carbamide peroxide, and mixtures thereof. Most preferred is hydrogen peroxide. Other materials suitable for use include materials which produce hydrogen peroxide when mixed with water, such as the percarbonates, specifically sodium percarbonate.

The peroxide is present in an amount of from about 0.01% to about 40%, by weight of the substance. The peroxide compound should provide an amount of hydrogen peroxide equivalent of from about 0.1% to about 20%, preferably from about 0.5% to about 10%, more preferably from about 1% to about 7%, and most preferably from about 2% to about 7% by weight of the substance. To deliver this amount of hydrogen peroxide equivalent, the peroxide compound, such as carbamide peroxide, is generally present in an amount of from about 0.1% to about 30% and preferably from about 3% to about 20%, by weight of the substance.

Additional materials that may be used with the peroxide include accelerating agents or bleach activators. Suitable bleach activators include trichloroisocyanuric acid and the phosphates, such as tetrasodium pyrophosphate.

Water is also present in the tooth whitening substance disclosed herein. Preferably, a high water content is desired to obtain the benefits described before. The water, employed in the present invention should, preferably, be deionized and free of organic impurities. Water comprises generally from about 0.1% to about 95%, preferably from about 5% to about 90%, and more preferably from about 10% to about 80%. The high water content tooth whitening substances will have a water content of greater than about 60%, preferably from about 65% to about 99%, more preferably from about 68% to about 95%, and most preferably from about 70% to about 90%, by weight of the total tooth whitening substance.. This amount of water includes the free water that is added plus that amount that is introduced with other materials.

The peroxide and water are contained in an aqueous substance. The tooth whitening substance is a high viscous matrix formed from gelling agents known in the art. Generally, these gelling agents are safe for oral use, typically do not readily dissolve in saliva, and do not react with or inactivate the oral care compounds incorporated into them. Commonly, the gelling agent is a swellable polymer. An effective amount of a gelling agent to enable the tooth whitening substance to form a is thin layer will vary with each type of gelling agent. The thin layer will have a viscosity and yield stress enabling the tooth whitening substance to form the thin layer on a substrate. The tooth whitening substance formed with these agents may also provide sufficient adhesive attachment of the film material to the targeted area of the mouth. For example, the level of gelling agent to form the tooth whitening substance composition with a carboxypolymethylene is from about 0.1% to about 15%, preferably from about 1% to about 10%, more preferably from about 2% to about 8%, and most preferably from about 3% to about 6%, by weight of the substance. An effective amount of a poloxamer gelling agent is from about 10% to about 40%, preferably from about 20% to about 35%, and more preferably from about 25% to about 30%, by weight of the substance.

Suitable gelling agents useful in the present invention include "Pemulen", made by B. F. Goodrich Company, carboxypolymethylene, carboxymethyl cellulose, carboxypropyl cellulose, hydroxyethyl cellulose, poloxamer, Laponite, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename "Carbopol". Particularly preferable Carbopols include Carbopol 934, 940, 941, 956, 971, 974, 980, and mixtures thereof. Particularly preferred is Carbopol 956. Carboxypolymethylene is a slightly acidic vinyl polymer with active carboxyl groups. The normal concentration of various carboxypolymethylene resins in water, according to the manufacturer, is below about 2%. However, it has been found that by preparing more concentrated carboxypolymethylene compositions having an absolute concentration in the ranges specified above, suitable high viscosity tooth whitening substance may be prepared.

The concentrated carboxypolymethylene gels have a number of important characteristics in addition to high viscosity. Enough carboxypolymethylene can be added to the tooth whitening substance beyond that required to provide high viscosity such that a significant quantity of saliva or water is required to lower the viscosity to the point that the composition may be diluted and washed out by saliva. The concentrated carboxypolymethylene composition also has a unique tackiness or stickiness which retains and seals the strip of material against the targeted oral cavity surface it is affixed to, particularly teeth. However, care should be taken to avoid too much carboxypolymethylene thereby making insertion or withdrawal of the strip material difficult.

While the gel described above may provide sufficient adhesiveness, additional gelling agents may also be included in the formula to help the peroxide adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

An additional carrier material may also be added to the substance. Carrier materials can be humectants, pH adjusting agents, stabilizing agents, desensitizing agent, and other components as listed below. Suitable stabilizing agents include benzoic acid, salicylic acid, butylated hydroxytoluene, tin salts, phosphates, and others. Suitable humectants include glycerin, sorbitol, polyethylene glycol, propylene glycol, and other edible polyhydric alcohols. Humectants are generally present in an amount of from about 10% to about 95% and more specifically from about 50% to about 80%. The high water content tooth whitening substances will have a lower humectant content. The humectants of these substances is less than about 39%, preferably from about 0% to about 35%, more preferably from about 1% to about 30%, and most preferably from about 5% to about 25%, by weight of the substance. In addition to the above materials of the gel of the present invention, a number of other carrier materials can also be added to the substance. Additional carriers include, but are not limited to, flavoring agents, sweetening agents such as saccharin, xylitol, opacifiers, coloring agents, and chelants such as ethylenediaminetetraacetic acid. These additional ingredients can also be used in place of the compounds disclosed above.

A pH adjusting agent may also be added to optimize the storage stability of the tooth whitening substance and to make the substance safe for oral tissues. These pH adjusting agents, or buffers, can be any material which is suitable to adjust the pH of the substance. Suitable materials include sodium bicarbonate, sodium phosphate, sodium hydroxide, ammonium hydroxide, potassium hydroxide, sodium stannate, triethanolamine, citric acid, hydrochloric acid, sodium citrate, and combinations thereof. The pH adjusting agents are added in sufficient amounts so as to adjust the pH of the gel composition to about 3 to about 10, preferably from about 4 to about 8.5, and more preferably from about 4.5 to about 8 pH adjusting agents are generally present in an amount of from about 0.01% to about 15% and preferably from about 0.05% to about 5%, by weight of the substance.

Desensitizing agents may also be used in the tooth whitening substance. These agents may be preferred for consumers who have sensitive teeth. Desensitizing agents include potassium nitrate, citric acid, citric acid salts, strontium chloride, and combinations thereof. Potassium nitrate is a preferred desensitizing agent. Other agents which provide the benefit of reduced tooth sensitivity are also included in the present invention. An effective amount of a desensitizing agent to reduced tooth sensitivity will be included. Typically, this amount is from about 0.01% to about 10%, preferably from about 0.1% to about 8%, and more preferably from about 1% to about 7% by weight of the tooth whitening substance.

Substrate

The tooth whitening substance will generally be on a substrate. A substrate, as used herein, means the surface or material that the tooth whitening substance is located on. Typically, the tooth whitening substance is stored on a substrate. The substrate may or may not be used to apply the tooth whitening substance to the teeth. The substrate includes any material or item that the tooth whitening substance may be placed on and which is substantially unreactive with the peroxide. Substrates include flexible and non-flexible materials, preformed items, and permanently deformable and not permanently deformable items. For example, a substrate maybe a counter top, glass, wood, plastic, or other hard material. Substrates that may be used to apply the tooth whitening substance to the teeth include preformed dental trays, flexible dental trays, strips of material, permanently deformable strips of material, wax, or any other implement used for applying a tooth whitening substance to the teeth.

Strip of Material

The strip of material is a preferred form of the substrate. A strip of material may be used to help apply the tooth whitening substance to the teeth. The strip of material serves as a protective barrier to substantially prevent saliva contacting the tooth whitening substance and leaching and/or erosion of the tooth whitening substance from the surface of the teeth by the wearer's lips, tongue, and other soft tissue. In order for an active in tooth whitening substance to act upon the surface of tooth over an extended period of time, from several minutes to several hours, it is important to minimize such leaching and/or erosion. The term "act upon" is herein defined as bringing about a desired change. If the substance is a tooth whitener, it bleaches color bodies to bring about whitening.

The strip of material is any substrate which is generally substantially planar through the cross-section or flat or curved when stored and can be used to apply the tooth whitening substance to the teeth. Although the strip of material may be curved, the strip of material does not form a trough and is not a typical dental tray. Preferably, the strip of material is not permanently deformable. The strip of material may comprise materials such as polymers, natural and synthetic wovens, non-wovens, foil, rubber, netting, and combinations thereof. The strip of material may be a single layer of material or a laminate of more than one layer. Generally, the strip of material is substantially water impermeable. The material may be any type of polymer that is compatible with the tooth whitening substance and particularly the peroxide. The material may comprise a single polymer or a mixtures of polymers. Suitable polymers include, but are not limited to, polyethylene, ethylvinylacetate, ethylvinyl alcohol, polyesters such as Mylar® manufactured by DuPont, fluoroplastics such as Teflon® manufactured by DuPont, polyvinyl alcohol, polypropylene, and combinations thereof. Preferably, the material is polyethylene. The strip of material is generally less than about 1 mm thick, preferably less than about 0.05 mm thick, and more preferably from about 0.001 to about 0.03 mm thick. A polyethylene strip of material is preferably less than about 0.1 mm thick and more preferably from about 0.005 to about 0.02 mm thick. The thickness and the permeability of the strip of material may have an effect on the stability of the tooth whitening substance. In general, a thicker strip may provide more stability for the tooth whitening substance. However, the thickness of the strip of material must be balanced with the consumer acceptance of comfort of wearing the strip. Preferably, the shape of the strip of material is any shape that has rounded corners. The strip of material is preferably of a size that individually fits the tooth or row of teeth desired to be bleached. Generally, this is the front 6–8 teeth of the upper or lower rows of teeth that are visible when the wearer is smiling. Optionally, the strip of material may fit the entire upper or lower rows of teeth when positioned against the teeth. The size of the strip of material depends upon many factors, including the number of teeth to be bleached, the size of the teeth, and personal preference of the wearer. In general, the length of the strip of material is from about 2 cm to about 12 cm and preferably from about 4 cm to about 9 cm. The width of the strip of material will also depend upon many factors, including whether or not the strip of material wraps around the teeth and covers both surfaces of the tooth. In a general application, the width of the strip of material is from about 0.5 cm to about 4 cm and preferably from about 1 cm to about 2 cm.

The strip of material may contain shallow pockets. When the tooth whitening substance is coated on a substance-coated side of strip of material, additional substance fills shallow pockets to provide reservoirs of additional substance. Additionally, the shallow pockets help to provide a texture to the delivery system. The film will preferably have an array of shallow pockets. Generally, the shallow pockets are approximately 0.4 mm across and 0.1 mm deep. When shallow pockets are included in the strip of material and substances are applied to it in various thicknesses, the overall thickness of the delivery system is generally less than about 1 mm. Preferably, the overall thickness is less than about 0.5 mm.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In a preferred embodiment but not required for the present invention, the strip of material has a flexural stiffness of less than about 5 grams/cm as measured on a Handle-O-Meter, model #211–300, available from Thwing-Albert Instrument Co. of Philadelphia, Pa., as per test method ASTM D2923–95. Preferably, the strip of material has a flexural stiffness less than about 4 grams/cm, more preferably less than about 3 grams/cm, and most preferably from about 0.1 grams/cm to about 1 grams/cm.

The preferred low stiffness enables the strip of material to drape over the contoured surfaces of teeth with very little force being exerted; that is, conformity to the curvature of the wearer's mouth and gaps between adjacent teeth is maintained because there is little residual force within strip of material to cause it to return to its substantially flat shape. The flexibility of the strip enables the strip of material to contact adjoining soft tissue over an extended period of time with minimal physical irritation. The strip of material does not require pressure forming it against the teeth.

The strip of material may also be readily conformable to tooth surfaces and to the interstitial tooth spaces without permanent deformation when the product is applied.

The strip of material is held in place on a tooth or a plurality of adjacent teeth by adhesive attachment. Generally, this is provided by the tooth whitening substance although it could be provided by other means. The viscosity and general tackiness of the substance cause the strip of material to be adhesively attached to the teeth without substantial slippage under the potential friction from the lips, tongue, and other soft tissue rubbing against the strip of material during mouth movements associated with talking, drinking, etc.

In a preferred embodiment, a peel force of from about 1 gram to about 50 grams for a 1.5 cm strip width (approximately 17 grams/cm) is all that is required to remove the strip of material from the teeth. Preferably, the peel force is from about 5 grams to about 40 grams and more preferably from about 10 grams to about 30 grams. The low peel force is desired for consumer handling purposes.

The strip of material may be formed by several of the fihn making processes known in the art. Preferably, a strip of material made of polyethylene is made by a blown process or a cast process. Processes, such as extrusion and other processes that do not affect the flexural rigidity of the strip of material, are also feasible. Additionally, the tooth whitening substance may be incorporated onto the strip during the processing of the strip. The substance may be a laminate on the strip.

Release Liner

If desired, a release liner may be used with the tooth whitening product. The release liner may be formed from any material which exhibits less affinity for substance than substance exhibits for itself and for the strip of material. The release liner preferably comprises a sheet of material such as polyethylene, paper, polyester, polypropylene, fluoropolymers such as Teflon®, or other material which may optionally be coated with a non-stick type material. The release liner material may be coated with silicone, fluoropolymers such as Teflon®, fluorosilicones, or other non-stick type materials. A preferred release liner is Scotchpak® 1022, produced by 3M.

The release liner may be attached to the side of the strip of material coated with the tooth whitening substance. The release liner may be cut to substantially the same size and shape as the strip of material or the release liner may be cut larger than the strip of material to provide a readily accessible means for separating the material from the strip. The release liner may be formed from a brittle material which cracks when the strip is flexed or from multiple pieces of material or a scored piece of material. Alternatively, the release liner may be in two overlapping pieces such as a typical adhesive strip bandage type design. A further description of materials suitable as release agents is found in Kirk-Othmer Encyclopedia of Chemical Technology, Fourth Edition, Volume 21, pp.207–218, incorporated herein by reference.

EXAMPLES

Examples of high water content tooth whitening substances are described in the tables below.

|  | 1 | 2 | 3 | 4 | 5 | 6 |
|---|---|---|---|---|---|---|
| Glycerin | 10.000% | 10.000% | 20.000% | 10.000% | — | — |
| Water | 67.776% | 64.348% | 54.348% | 64.248% | 74.148% | 67.776% |
| Hydrogen Peroxide (35% Solution) | 15.143% | 18.571% | 18.571% | 18.571% | 18.571% | 15.143% |
| Carboxypolymethylene | 4.500% | 4.500% | 4.500% | 4.500% | 4.500% | 4.500% |
| Sodium Hydroxide (50% Solution) | 2.000% | 2.000% | 2.000% | 2.000% | 2.000% | 2.000% |
| Sodium Saccharin | — | — | — | 0.100% | 0.200% | — |
| Sodium Stannate | 0.200% | 0.200% | 0.200% | 0.200% | 0.200% | 0.200% |
| Sodium Pyrophosphate | 0.381% | 0.381% | 0.381% | 0.381% | 0.381% | 0.381% |
| Propylene Glycol | — | — | — | — | — | 10.000% |
| Pluronic 407 | — | — | — | — | — | — |

|  | 7 | 8 | 9 | 10 | 11 | 12 |
|---|---|---|---|---|---|---|
| Glycerin | 10.000% | — | 3.000% | 15.000% | 10.000% | 10.000% |
| Water | 68.157% | 57.276% | 72.576% | 63.076% | 72.919% | 66.955% |
| Hydrogen Peroxide (35% Solution) | 15.143% | 15.143% | 17.143% | 15.143% | — | 17.143% |
| Carboxypolymethylene | 4.500% | — | 4.500% | 4.500% | 4.500% | 4.500% |
| Sodium Hydroxide (50% Solution) | 2.000% | 2.000% | 2.200% | 1.700% | 2.000% | — |
| Sodium Saccharin | — | — | — | — | — | — |
| Sodium Stannate | 0.200% | 0.200% | 0.200% | 0.200% | 0.200% | — |
| Sodium Pyrophosphate | — | 0.381% | 0.381% | 0.381% | 0.381% | — |
| Propylene Glycol | — | — | — | — | — | — |
| Pluronic 407 | — | 25.000% | — | — | — | — |
| Potassium Hydroxide | — | — | — | — | — | 1.403% |
| Carbamide Peroxide | — | — | — | — | 10.000% | — |

All ingredients in the tooth whitening substances should be mixed until homogeneous.

Method of Use in the Oral Cavity

When using the stable tooth whitening substance in the oral cavity, a substrate with the stable tooth whitening substance may be applied by the wearer to one tooth or a plurality of adjacent teeth. Preferably, the substrate is a strip of material. The strip of material may also cover adjacent soft tissue. The side of the material facing the teeth is coated with a tooth whitening substance which is preferably in a viscous state to provide not only the peroxide but also tackiness between the tooth surfaces and the strip of material to hold the strip in place for an extended period of time. The strip of material readily conforms to the teeth by lightly pressing it against the teeth and/or by the wearer gently sucking through the gaps between the teeth. The strip of material is easily removed by the wearer by peeling it off. Preferably, each successive treatment will use a fresh strip of material.

The tooth surface is not required to be prepared before the prodouct is applied. For example, the wearer may or may not choose to brush his teeth or rinse his mouth before applying the delivery system. The surfaces of the teeth are not required to be dried or to be excessively wet with saliva or water before the strip of material is applied.

Preferably, the substrate and tooth whitening substance are substantially transparent so as to be almost unnoticeable when worn.

Preferably, the wearer applies the product to the teeth continuously for about 5 minutes to about 120 minutes a day, preferably from about 30 minutes to about 60 minutes. Generally, this is done once or twice a day for about 7 to 28 days. The amount of time and the number of days are dependent upon several factors, including the amount of bleaching desired, the wearer's teeth, and if initial or maintenance bleaching is desired. The bleaching is done to achieve a whitening benefit of about 2 to about 12 shade guide improvement as measured by VITA LUMIN® Vacuum Farbskala Shade Guides, a product of VITA Zahnfabrik, of BadSackingen, Germany. The whitening effect can also be measured through photometric methods known in the art.

When the wearer removes the strip of material from the tooth, there may be a residue of substance remaining on the surface. This residual will not be great, as the tooth whitening substance has affinity for both the film and for itself. If residual substance remains, it may be easily removed by brushing or rinsing.

Method of Testing

After the tooth whitening substance is manufactured, it will be stored as a thin layer. Typically this thin layer of tooth whitening substance will be on a substrate or strip of material. Alternatively, the thin layer of tooth whitening substance could be stored on any material, such as coated on the bottom of container. If desired, a release liner may be applied on top of the tooth whitening substance.

The strip of material with the thin layer of tooth whitening substance will be stored in a some type of closed container. The closed container may be a pouch, box, plastic container, envelope, bag, or other suitable container of any shape or size. The container should be made of a material that is not translucent, has low or no moisture permeability, and is generally impermeable. The container may be made of one or more materials and may optionally have a liner. For example, a pouch could be made of foil and have a polyethylene lining. Other suitable materials that are not translucent and prevent moisture permeability include plastic, paper, foil, cardboard, polymers, and rubbers. Generally, the head space in the container containing the thin layer of tooth whitening substance should be controlled. The head space is measured as the empty volume in the container. The ratio of head space to volume of tooth whitening substance should be less than about 500, preferably less than 400, more preferably from about 0.5 to about 200, and most preferably from about 1 to about 100.

During storage of the thin layer of tooth whitening substance, the temperature should remain at room temperature, approximately 25° C. After the desired amount of time, the peroxide concentration is measured using the Iodoetric titration method. The Iodometric titration method is a standard method for measuring peroxide concentration. In general, the method is performed by weighing the strip and gel, dissolving the gel in 1M sulfric acid, and reacting the peroxide with an excess of potassium iodide in the presence of ammonium molybdate. This is then titrated with a known concentration of sodium thiosulfate to a clear endpoint using a starch indicator. The strip is weighed upon completion of the titration and the gel weight is determined by difference. The peroxide concentration in the gel is then calculated.

As described before, the peroxide level testing is done about three months after manufacture. Stability testing for peroxide could be at any other time point, such as four months or six months after manufacture, for a more stringent stability test. As described before, stable means that the peroxide in the tooth whitening substance maintains at least 80% of its original amount when stored as a thin layer for about three months after manufacture. Preferable, a stable tooth whitening substance will have a peroxide concentration of about 85% and more preferably about 90% of its original amount about three months after manufacture.

Peroxide level testing may be performed at a variety of times depending upon stability requirements and conditions. For example, the peroxide level may be tested at 7, 14, 21, 30, 42, 60, 90, 120, 150, and 180 days after manufacture. The storage of the stable tooth whitening substance may be at 25° C., 40° C., or other suitable temperatures. Typically, the relative humidity is at 60%.

While particular embodiments of the present invention have been illustrated and described, it will be obvious to those skilled in the art that various changes and modifications may be made without departing from the spirit and scope of the invention. and it is intended to cover in the appended claims all such modifications that are within the scope of the invention.

What is claimed is:

1. A tooth whitening product, comprising:
  a flexible strip of material which is conformable to tooth surfaces without permanent deformation; and
  a thin layer of a tooth whitening substance in contact with said flexible strip of material, wherein said tooth whitening substance comprises between 54.348% and 74.148% water, from about 0.1% to about 20% peroxide, an effective amount of a gelling agent to enable the tooth whitening substance to form said thin layer, and from about 0.1% to about 39% carrier materials.

2. The product of claim 1 wherein the thin layer of tooth whitening substance is less than about 3 millimeters thick.

3. The product of claim 1 wherein the peroxide maintains at least about 80% of its original amount about three months after manufacture.

4. The product of claim 1 further comprising less than about 39% of total humectant.

5. The product of claim 4 wherein the humectant is glycerine and is present in an amount of less than about 35%.

6. The product of claim 1 wherein the strip of material is a material selected from the group consisting of polyethylene, polyester, polypropylene, and combinations thereof.

7. The product of claim 1 further comprising a pH adjusting agent.

8. The product of claim 1 wherein the thin layer of tooth whitening substance has a surface area to volume ratio of greater than about 0.6 millimeter$^{-1}$.

9. The product of claim 1, wherein said tooth whitening substance comprises between about 65% and about 99% water.

10. The product of claim 1, wherein said tooth whitening substance comprises between about 70% and about 90% water.

11. The product of claim 1, wherein said flexible strip of material has pockets.

12. The product of claim 11, wherein said pockets are about 0.4 mm across.

13. The product of claim 12, wherein said pockets have a depth of about 1 mm.

14. The product of claim 1, wherein said flexible strip of material has a thickness less than about 1 mm.

15. The product of claim 1, wherein said flexible strip of material has a thickness less than about 0.05 mm.

16. The product of claim 1, wherein said flexible strip of material has a thickness between about 0.001 mm and about 0.03 mm.

17. The product of claim 1, wherein said flexible strip of material is substantially planar.

18. The product of claim 1, wherein said flexible strip of material has a length between about 2 cm and about 12 cm.

19. The product of claim 18, wherein said flexible strip of material has a width between about 0.5 cm and about 4 cm.

20. The product of claim 1, wherein the amount of said tooth whitening substance is less than about 0.2 gms/cm$^2$.

21. The product of claim 1, wherein the amount of said tooth whitening substance is between about 0.005 gms/cm$^2$ and about 0.1 gms/cm$^2$.

22. The product of claim 1, wherein said strip of material has a flexural stiffness of less than about 5 gms/cm.

23. The product of claim 1, wherein said strip of material has a flexural stiffness between about 0.1 gm/cm and about 1 gm/cm.

24. A method of tooth whitening, comprising:
  inserting a flexible strip of material into a human user's mouth;
  conforming said flexible strip of material to tooth surfaces of said human user's mouth; and
  wherein said flexible strip of material has a thin layer of a tooth whitening substance in contact with said flexible strip of material and wherein said tooth whitening substance comprises between 54.348% and 74.148% water, from about 0.1% to about 20% peroxide, an effective amount of a gelling agent to enable the tooth whitening substance to form said thin layer, and from about 0.1% to about 39% carrier materials.

25. The method of claim 24, wherein said flexible strip of material is substantially flat before said step of conforming said flexible strip of material to said front surface of said plurality of teeth.

26. The method of claim 24, wherein said tooth whitening substance comprises between about 65% and about 99% water.

27. The method of claim 24, wherein said tooth whitening substance comprises between about 70% and about 90% water.

28. The method of claim 24, wherein said flexible strip of material has pockets.

29. The method of claim 28, wherein said pockets are about 0.4 mm across.

30. The method of claim 29, wherein said pockets have a depth of about 1 mm.

31. The method of claim 24, wherein said flexible strip of material has a thickness less than about 1 mm.

32. The method of claim 24, wherein said flexible strip of material has a thickness less than about 0.05 mm.

33. The method of claim 24, wherein said flexible strip of material has a thickness between about 0.001 mm and about 0.03 mm.

34. The method of claim 24, wherein said flexible strip of material is substantially planar.

35. The method of claim 24, wherein said flexible strip of material has a length between about 2 cm and about 12 cm.

36. The method of claim 35, wherein said flexible strip of material has a width between about 0.5 cm and about 4 cm.

37. The method of claim 24, wherein the amount of said tooth whitening substance is less than about 0.2 gms/cm$^2$.

38. The method of claim 24, wherein the amount of said tooth whitening substance is between about 0.005 gms/cm$^2$ and about 0.1 gms/cm$^2$.

39. The method of claim 24, wherein said strip of material has a flexural stiffness of less than about 5 gms/cm.

40. The method of claim 24, wherein said strip of material has a flexural stiffness between about 0.1 gm/cm and about 1 gm/cm.

41. A method of tooth whitening, comprising:

inserting a flexible strip of material into a human user's mouth;

conforming said flexible strip of material to tooth surfaces of said human user's mouth without permanent deform; and wherein said flexible strip of material has a thin layer of a tooth whitening substance in contact with said flexible strip of material and wherein said tooth whitening substance comprises between 54.348% and 74.148% water, from about 0.1% to about 20% peroxide, an effective amount of a gelling agent to enable the tooth whitening substance to form said thin layer, and from about 0.1% to about 39% carrier materials.

* * * * *